United States Patent [19]
Takemura et al.

[11] Patent Number: 5,223,230
[45] Date of Patent: Jun. 29, 1993

[54] COMPONENT FOR DEODORIZING AIR AND OTHER GASES

[75] Inventors: Yozo Takemura, Tokyo; Tamio Noda, Tokai; Yoshitsugu Sakagami; Tadashi Morita, both of Osaka, all of Japan

[73] Assignees: Nippon Steel Corporation, Tokyo; Matsushita Electric Works, Ltd., Kadoma, both of Japan

[21] Appl. No.: 658,800

[22] Filed: Feb. 25, 1991

[51] Int. Cl.$^5$ ............................ A61L 9/01; A61L 9/00
[52] U.S. Cl. ......................................... 422/122; 422/4; 422/5; 422/120; 424/76.2; 424/76.21
[58] Field of Search ....................... 422/4, 5, 120, 122; 424/76.2, 76.21

[56] References Cited
FOREIGN PATENT DOCUMENTS 59-132937 7/1984 Japan .
3274630 11/1988 Japan ................................. 424/76.2

Primary Examiner—Robert J. Warden
Assistant Examiner—Stephanie Blythe
Attorney, Agent, or Firm—Cushman, Darby and Cushman

[57] ABSTRACT

A component for deodorizing air or gas having a coexist compound as a deodorizing element, said coexist compound comprising a metal and a reaction product of the metal and an acid, wherein the metal is selected from at least one of Fe, Mn, Cr, Ni, Zn, Al and Cu, and the acid is selected from at least one of ascorbic acid, gluconic acid, citric acid, tartaric acid, tannic acid, gallic acid, EDTA and malic acid, wherein clean air or gas is passed through the deodorizing element to restore its deodorizing effect after a period of time sufficient for the deodorizing element to lose its deodorizing power.

20 Claims, 4 Drawing Sheets

NH₃ CONCENTRATION AFTER TREATMENT (ppm)

NH₃ CONCENTRATION AFTER TREATMENT (ppm)

NH₃ CONCENTRATION AFTER TREATMENT (ppm)

NH₃ CONCENTRATION AFTER TREATMENT (ppm)

NH₃ CONCENTRATION AFTER TREATMENT (ppm)

COMPONENT FOR DEODORIZING AIR AND OTHER GASES

BACKGROUND OF THE INVENTION

1. Field of the Invention

The present invention relates to a component for deodorizing air and other gases.

2. Background Information

There are known a number of components for deodorizing air or other gases, including those containing active carbon which absorbs odorous substances, and those containing a chemical agent which emits a fragrance to conceal the existing odor. However, these deodorants cannot destroy the existing odorous substance and the deodorizing effect is saturated or diminished within in a short period of time.

Japanese Patent Application No. 59-132937 relates to a powdered complex having a deodorizing effect. This application discloses a powdered complex mixture obtained by drying a solution produced by reacting an L-ascorbic acid solution with a ferrous salt solution such as $FeSO_4$ $FeCl_2$ $Fe(NO_3)_2$ solution. This powdered complex mixture reacts with an odorous substance to change its chemical structure. However, the powdered complex mixture simultaneously undergoes chemical changes in this reaction, and loses its odorizing power in a short period of time.

Clearly, a deodorizing component in which the deodorizing agent can be revitalized easily and simply whenever its deodorizing effect is diminished would be advantageous, as that would reduce the troublesome procedure of replacing the deodorizing agent.

SUMMARY OF THE INVENTION

It is therefore an object of the present invention to provide a component for deodorizing air or other gases having a powerful deodorizing element and an easy means to revitalize the deodorizing power of the element so that the component can be used for a much longer period of time than any known component without the need to replace the deodorizing element.

According to the present invention, a coexist compound containing a particular metal and the reaction product of the particular metal and a particular acid solution is used as the deodorizing element. The metal is selected from Fe, Mn, Cr, Ni, Zn, and Al and the acid solution is selected from ascorbic acid, gluconic acid, citric acid, tartaric acid, tannic acid, gallic acid, EDTA and malic acid. The metal and the acid solution are contacted with each other and react chemically with each other.

Using this process, the coexist compound containing a particular metal and a reaction product of the particular metal and the particular acid can be obtained. The coexist compound of the present invention differs from the composition of the powdered complex shown in Japanese Patent Application No. 59-132937 described above in that the coexist compound of the present invention contains unreacted metal in its composition. The coexist compound of the present invention has a deodorizing effect similar to those of the powdered complexes of the prior art. However, in contrast to the powdered complex of the prior art, the deodorizing effect of the coexist compound of the present invention can be revitalized easily when the deodorizing power is decreased or lost with use over a long period of time. In the coexist compound of the present invention, the revitalization of the deodorizing effect can be achieved in a short period of time by passing clean air or another gas through the deodorizing element.

The deodorizing power of the element in treating $H_2S$ containing gas, for example, can be strengthened by incorporating a basic salt into the coexist compound. Examples of basic salts which can be used include CaO, MgO, $Ca(OH)_2$, $Mg(OH)_2$, $CaCO_2$, $MgCO_3$ and $Na_2CO_3$. An ordinary deodorizing compound containing active carbon can be used together with the deodorizing element of the present invention. In producing the deodorizing element of the present invention, it is preferable to use as the metal a porous metal block obtained by sintering and having numerous pores passing through it. An electric resistance heater or an electromagnetic induction heater can be used to heat the deodorizing element during revitalization.

BRIEF DESCRIPTION OF THE DRAWINGS

FIG. 1 illustrates results of experiments comparing the present invention with the prior art.

DETAILED DESCRIPTION OF THE PREFERRED EMBODIMENTS

The present inventors used an iron powder and a porous block of urethane foam to produce a porous block of iron. A slurry was prepared by mixing iron powder with a paste liquid. The urethane block was placed into the slurry and then removed. By this process, all the skeleton composing the urethane foam was covered with the slurry. Then the urethane block was heated and sintered. By this heating and sintering, the urethane was decomposed and eliminated, leaving a porous block of sintered iron. This porous block of sintered iron was then immersed in an ascorbic acid solution, and the surface of the sintered iron was reacted with the ascorbic acid. Then the porous block was removed from the solution and dried. By this process, all iron skeleton composing pores of the sintered iron was covered by the reaction product of the iron and ascorbic acid. The coexist compound of iron and the reaction product of iron and ascorbic acid, thus obtained, was used as a deodorizing element in the following experiment.

In examining the deodorizing effect of this new element, it was found that this coexist compound has a powerful deodorizing effect similar to those of the powdered complex shown in Japanese Patent Application No. 59-132937, and that this coexist compound can destroy harmful gases including $SO_x$, $NO_x$, CO, $CO_2$ and acetaldehyde. It was also found that, although this new element gradually loses its deodorizing effect when it is used for a long period of time, it regains the deodorizing effect by simply exposing it to flowing air for a short period of time or, more simply, by leaving it alone in the ordinary atmosphere for several days.

Figure 2:
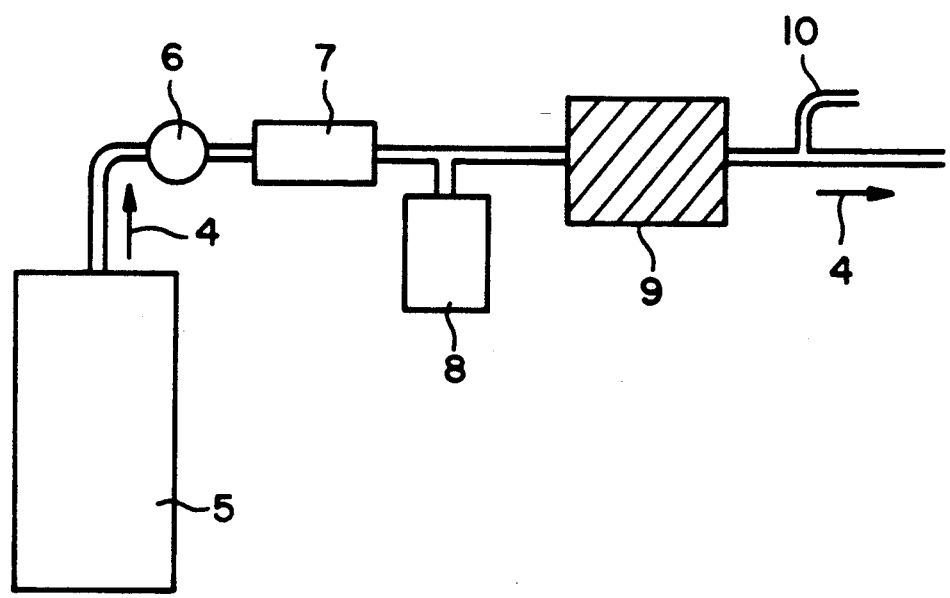
FIG. 2 illustrates a test apparatus of the present invention.

In an experiment, the inventors used a test assembly as illustrated in FIG. 2, where container 9 was filled with a deodorant, and air containing $NH_3$ at a concentration of 100 ppm was blown out of gas cylinder 5. Arrows 4 show the flow direction of the gas, the amount, temperature and moisture of which were controlled by elements 6,7 and 8 respectively. The $NH_3$ concentration of the air after passing it through the container 9 was then measured. Treated gas was sampled via pipe 10.

Figure 1A:
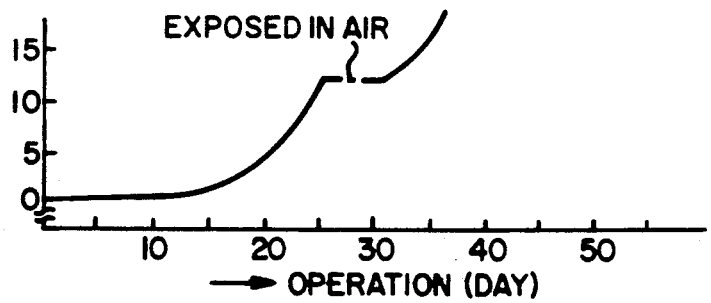
FIG. 1(A) shows the results of experiments using the powdered complex described in Japanese Patent Application No. 59-132937.

FIG. 1(A) illustrates a result of the experiment on the powdered complex described in the above-cited Japanese Patent Application. As is apparent from FIG. 1(A), the known deodorant was highly effective for the first 15 days of use, but thereafter rapidly lost its effect, becoming almost ineffective in 25 days. After having been used for 25 days, the deodorant was removed from the container and exposed to fresh air for 5 days. Then the deodorant was placed back in the container and the same experiment was performed again. However, as shown in FIG. 1(A), the known deodorant never regained its deodorizing effect, thus showing its limited service life.

Figure 1B:
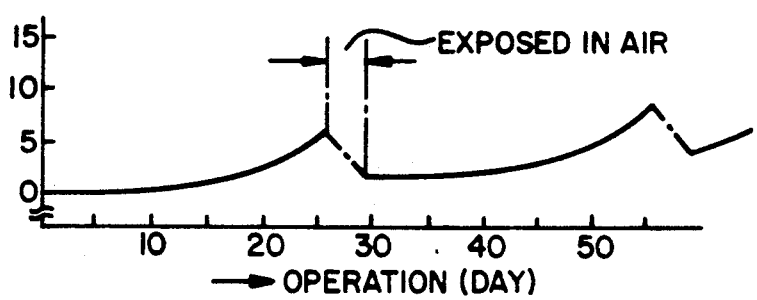
FIGS. 1(B)-(E) show the results of experiments using the present deodorizing element.

FIG. 1(B) shows the deodorizing effect of the deodorizing element of the present invention. As in the case of FIG. 1(A), the deodorizing element gradually loses its effect after the first 15 days of service. The inventors removed the deodorizing element from the container after it had been used for 25 days and exposed it to fresh air for 5 days. The deodorizing element was then put to use again, as in the case of FIG. 1(A). As shown in FIG. 1(B), exposure to the fresh air restored the deodorizing effect of the element, which was almost as effective as it had been in the initial stage of use. However, it is considered that a period of 5 days to regain its deodorizing effect is too long and thus the deodorizing element is not adequate for use in a continuously operating apparatus.

Figure 1C:
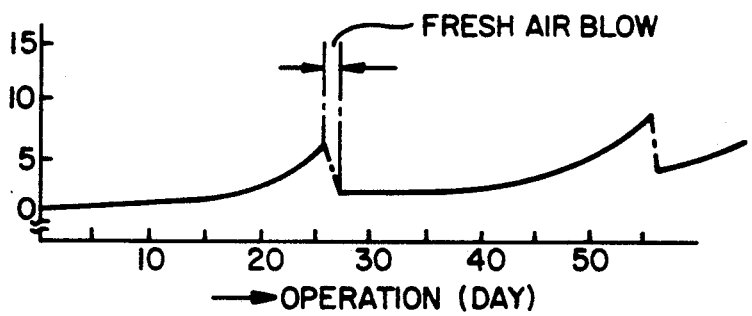

FIG. 1(C) shows another aspect of the deodorizing effect of the deodorizing element of the present invention. In FIG. 1(C), after the element had been used for 25 days, the gas cylinder 5 of FIG. 2 was removed and fresh air was passed through the container for 5 minutes. It was found that the deodorizing effect was restored almost to the initial level in this case. Thus, this revitalizing method to restore the deodorizing effect is very suitable for the deodorizing element in a continuously operating apparatus, as a 5 minute period of time necessary to regain its effect is not expected to cause a serious problem in a continuous operation.

Figure 1D:
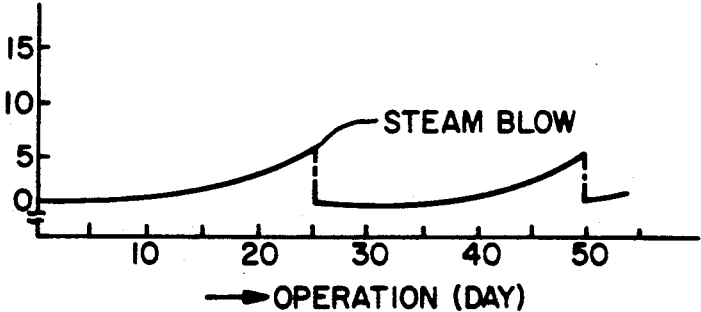

FIG. 1(D) shows still another aspect of the deodorizing effect of the present invention. In this case, after it had been used for 25 days, steam having a temperature of approximately 80° C. was passed through the container for several minutes. It was found that the deodorizing effect was almost fully restored. Thus, heating and/or moistening of the deodorizing element of the present invention is a very suitable method to restore its deodorizing effect.

Figure 1E:
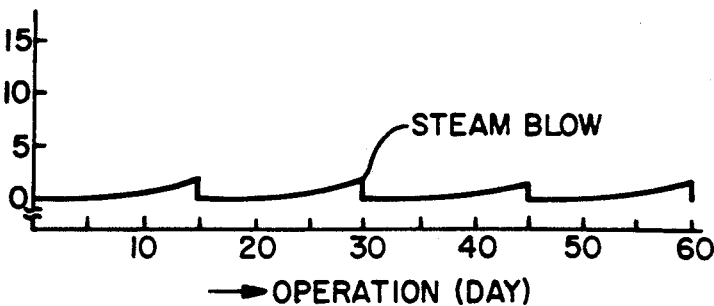

FIG. 1(E) shows yet another aspect of the deodorizing effect of the present invention. In this case, steam was periodically passed through the container once in every 15 days. The deodorizing effect did not significantly decline in 15 days and therefore the deodorizing element of the present invention regained its effect with a very short exposure to steam. Thus, periodic exposure to steam can greatly extend the service life of the deodorizing element.

The inventors conducted similar experiments substituting $H_2S$, $SO_x$, $NO_x$, $CO$, $CO_2$, acetaldehyde and other gases for NH, gas, and found that the coexist compound of the present invention has a strong deodorizing effect on these gases and can regain its air cleaning effect quickly by passing fresh air through the coexist compound, and optionally heating and/or moistening the coexist compound.

The inventors have also prepared a coexist compound containing metallic Mn and a reaction product of Mn and ascorbic acid using powdered Mn in place of iron powder. The deodorizing effect of the coexist compound was also examined and it was proved that this coexist compound was as effective for ammonia gas as the iron type coexist compound, and more effective for hydrogen sulfide gas than the iron type coexist compound. When the Mn type coexist compound partially loses its deodorizing effect after a long period of use, it can be revitalized for a short period of time by treatment with fresh air, hot air and moistened air or by moistening or heating the coexist compound in the same way as for the iron type coexist compound.

By conducting a similar experiment using Cr, Ni, Zn, Al and Cu in place of Fe and Mn, the inventors found that a coexist compound containing Al or Ni is as effective as one containing iron, and that a coexist compound containing Cr, Zn or Cu is not as effective as one containing iron. Also the inventors found that the deodorizing effect of all of these coexist compounds can be restored in the same manner as for the iron type coexist compound.

The inventors also conducted experiments using various acids including gluconic acid, citric acid, tartaric acid, tannic acid, gallic acid, EDTA and malic acid in place of ascorbic acid. As a result of the experiments, it was found that gluconic acid, citric acid, tartaric acid, tannic acid and gallic acid are as effective as ascorbic acid in producing an excellent coexist compound that can be fully revitalized in a similar manner as in the case of an ascorbic acid type coexit compound, while EDTA and malic acid are not as effective in that sense and can be fully revitalized in a similar manner.

The Fe, Mn, Cr, Ni, Zn, Al and Cu used in producing the deodorizing element need not be in a pure metal form. Metals containing the usual impure elements can be used. Also a mixture or an alloy of these metals can be used.

The metal used for producing the deodorizing element is not necessarily in the form of a porous block. A metal other than a porous block, for example, a pebble-sized metal or a grain-sized metal can also be used for this purpose. However, a porous metal block having numerous pores passing through it in random directions is preferred, because a coexist compound prepared from this porous metal block is in a porous shape which enables air and gas to contact closely with the deodorizing compound and pass easily through the deodorizing elements. This porous metal block can easily be obtained by sintering process, as described above.

Ascorbic acid, gluconic acid, citric acid, tartaric acid, tannic acid, gallic acid, EDTA and malic acid, as referred to in this specification, are meant to include acids having a concentration and purity sufficient to form a reaction product with the above-identified metals. Therefore an acid having the usual concentration and usual purity can be used.

Clean air or gas, as referred to in this specification, are meant to include air or gas which is clean enough to restore the deodorizing effect of the deodorizing element.

The inventors also found that the power to decompose $H_2S$ gas can be enhanced remarkably by incorporating a basic salt in the coexist compound of the present invention. One or more than one basic salt selected from $CaO$, $Mgo$, $Ca(OH)_2$, $Mg(OH)_2$, $CaCO_2$, $MGCO_3$ and $Na_2CO_3$ can be used for this purpose.

The inventors have provided an emulsion by mixing a powder of the basic salt and organic solvent, and this emulsion was sprayed on the surface of the coexist compound. Using this process, the deodorizing effect of the coexist compound in destroying the odorous substance of $H_2S$ has been improved remarkably.

A typical process of preparing a deodorizing element according to the present invention is described below.

A powdered iron having a size smaller than 10 µm was obtained by crushing pig iron in a wet process. The powdered iron was mixed with a binding solution containing carboxylmethylcellulose to obtain a slurry. A porous block of urethane foam was provided. The slurry was placed onto the skeleton of the urethane foam. Then the urethane block was heated. By this heating, the urethane was eliminated, the slurry was sintered, and a porous block of sintered iron having numerous pores passing through it was obtained. This iron block was immersed in an ascorbic acid solution having a concentration of 1 mol for 30 minutes. Then the iron block was removed and dried to produce a porous block of a deodorizing element in which a reaction product of iron and ascorbic acid coexisted with the iron. While this deodorizing element may be used without further treatment, its deodorizing effect can be strengthened by incorporating into its surface a basic salt.

In this deodorizing element, the gas flows through the numerous pores of the porous block and, since the reaction product of iron and ascorbic acid are placed on the surface of the pore, the gas is brought into sufficient contact with the reaction product so that the odor component of the gas may be fully eliminated.

In the present invention, clean or heated or moistened air or gas is supplied or the deodorizing element is heated or moistened for a short period of time regularly or periodically or whenever necessary. By this process, the deodorizing power of the element is revitalized regularly or periodically or whenever necessary during the operation.

When the apparatus is used to process a massive amount of gas containing odorous substances at a high concentration, the deodorant will be rapidly consumed. Therefore, in such a case, it is preferable to perform a revitalizing treatment regularly or periodically at short intervals.

On the other hand, when the apparatus is used to process a small amount of gas containing an odorous substance at a low concentration, the deodorant will not be consumed for a long time. Therefore, in this case, it is preferable to perform a revitalizing treatment whenever necessary.

When the deodorizing element is moistened, the moisture should be supplied carefully so that the moisture will not form dew drops and fall down from the element. In the present invention, odorous substance contained in air or gas are chemically decomposed by the reaction product of the metal and the metal and acid, and the reaction product is water soluble. Therefore, when too much moisture is supplied and dew drops form, the reaction product will dissolve in the dew drops and be lost as they fall from the deodorizing element.

Since the deodorizing element of the present invention contains free metal as a component, the deodorizing element can be heated using an electric resistance heater, an electromagnetic induction heater or similar electric heating means.

Figure 3A:
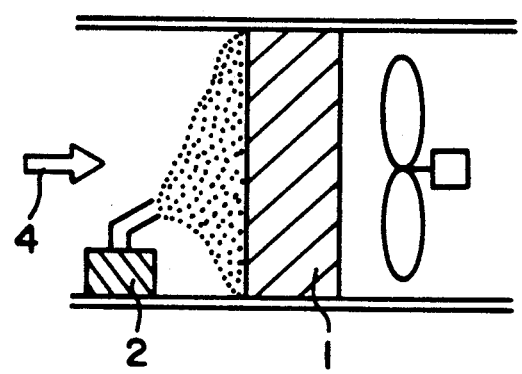
FIG. 3 illustrates examples of arrangements for moistening and heating the deodorizing element of the present invention.
Figure 3B:
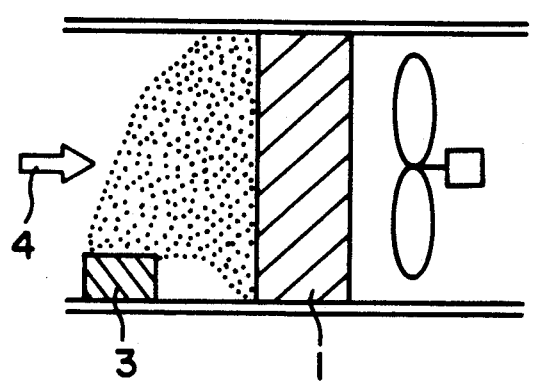
Figure 3C:
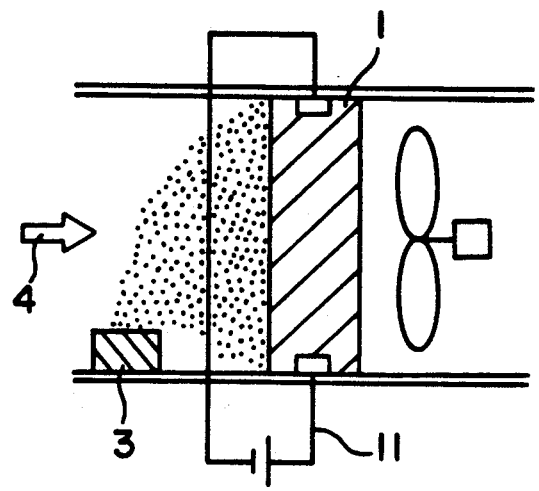

FIGS. 3(A) through 3(C) illustrate examples of arrangements for moistening and heating the deodorizing element. Numeral 1 denotes a deodorizing element, 2 an ultrasonic humidifier, 3 a heater-steam generator, 11 a heater for heating a deodorizing element. Odorous gas flows and passes through the deodorizing element in the direction indicated by arrow 4. When an ultrasonic humidifier or a heater-steam generator is arranged at the inlet side and air containing water particles less than 100 µm in diameter is supplied to the deodorizing element, as in the case of FIG. 3(A) and FIG. 3(B), the deodorizing element will be evenly moistened with no problems. FIG. 3(C) shows an arrangement where moistening and heating are conducted simultaneously. FIG. 3(D) illustrates a case where only clean air, shown as numeral 12, is supplied to revitalize the deodorizing element, without heating or moistening.

In contrast to the powdered complex shown in Japanese Patent Application 59-132937 where the deodorizing effect cannot be revitalized, the deodorizing effect of the deodorizing element of the present invention can be revitalized easily. Although the exact reasons for this difference are not entirely clear, some explanation can be made.

The deodorizing element of the present invention comprises a metal and its reaction product. The reaction product in the present invention is believed to have similar characteristics to that of the powdered complex of the prior art. Therefore the reaction product of the present invention may react with odorous substances in a similar manner as the powdered complex of the prior art and may produce a similar resultant chemical substance as that of the powdered complex of the prior art. In this reaction with an odorous substance, the reaction product of the present invention as well as the powdered complex of the prior art may be equally consumed and the deodorizing effect may equally decrease.

The deodorizing effect of the resultant chemical substance as described above cannot be revitalized by merely introducing fresh air or heating or moistening. However, the resultant chemical substance may be revitalized when it is contacted with a free metal. Therefore, in the case of the deodorizing element of the present invention which contains free metal, the deodorizing effect can be revitalized. However, in the case of the powdered complex of the prior art which does not contain any free metal, the deodorizing effect cannot be revitalized.

In the present invention, the deodorizing effect can be revitalized in a much shorter period of time by heating or moistening, rather than simply exposing the deodorizing element to the atmosphere. The exact reasons for this difference are not entirely clear. However, it is the inventors' belief that the contact of the resultant chemical substance described above with the metal is accelerated by heating or moistening, and the chemical reaction necessary to revitalize the deodorizing effect is achieved in a shorter period of time by heating or moistening.

The component of the present invention may comprise a deodorizing compound of active carbon, along with the coexist compound previously described. The deodorizing compound of active carbon includes an absorption active carbon such as a powdered active carbon, a fibrous active carbon and active carbon prepared from coconut shell.

The active carbon compound can be used as an independent deodorizing element. It can also be mixed with the coexist compound. There are odorous substances such as trichloroethylene and other organic chlorides that cannot be removed by chemical reaction with a deodorant. By including an active carbon compound with the coexist compound, the scope of the use of the deodorizing apparatus can be extended remarkably. In addition, with such a combination, ammonia and hydrogen sulphide absorbed in the active carbon compound can be processed further by the coexist compound. Thus, with the combined use of an active carbon compound, the deodorizing efficiency and the life of the active carbon compound can also be improved.

Figure 4:
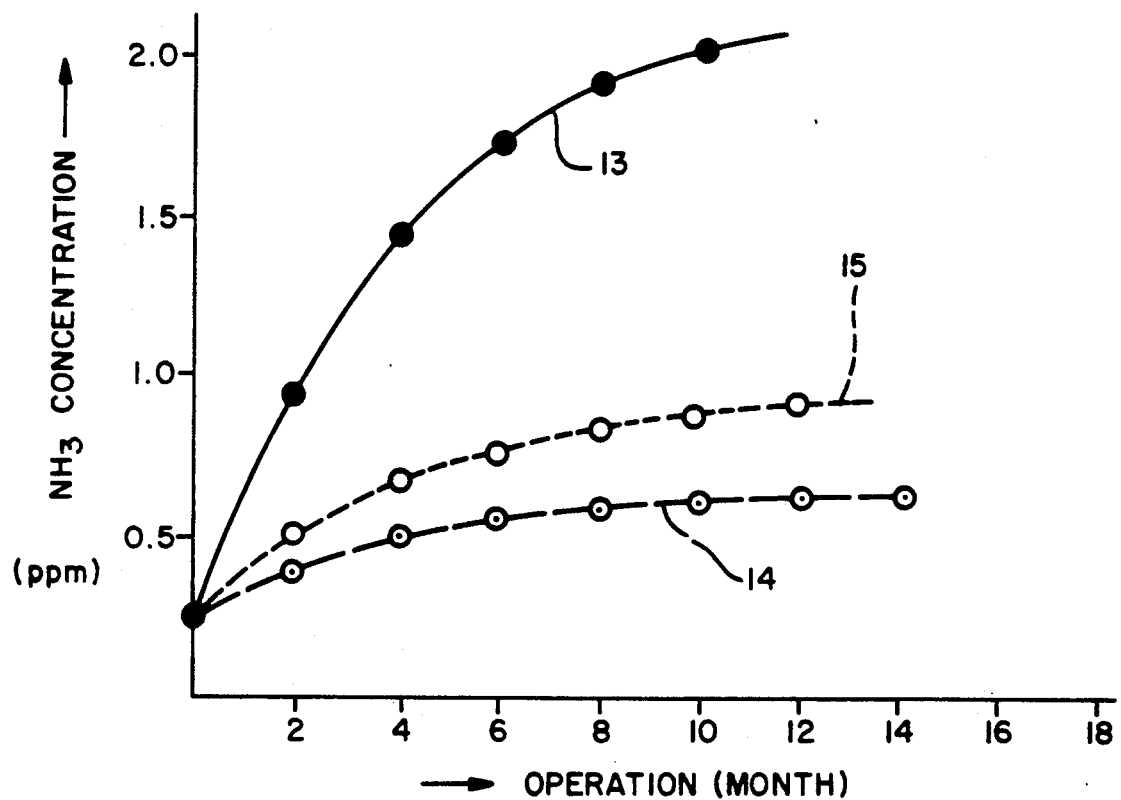
FIG. 4 illustrates the performance of the deodorizing element of the present invention.

Another embodiment of the present invention is described below. Powdered iron and powdered manganese having an average particle size of 10 $\mu$m were mixed at a ratio of Fe:Mn=80:20 by weight, and a slurry was prepared from the mixture using a carboxymethylcellulose aqueous solution. The slurry was then applied to the surface of a porous block of urethane foam having dimensions of 200 mm $\times$ 200 mm $\times$ 10 mm and an average pore diameter of about 1 mm. The block of urethane foam was then subjected to heating at about 1200° C., by which urethane was burnt and dissipated, leaving a porous block of sintered iron having numerous pores passing through it in random directions. The porous sintered block was then immersed in a 1 mol L-ascorbic aid solution for 30 minutes to produce a coexist compound of the present invention. The coexist compound was then basically treated by spraying an emulsion of $Na_2CO_3$ and methylalcohol to obtain the deodorizing element of the present invention. The deodorizing element was set in a component or unit and the component was arranged in a lavatory to observe its performance. Line 13 of FIG. 4 shows its performance when no treatment for revitalizing the deodorizing element was performed. Line 14 of FIG. 4 shows its performance when wet fresh air at a temperature of 80° C. was supplied to the deodorizing element periodically for 1 minute in every 24 hours. Line 15 of FIG. 5 shows its performance when the deodorizing element was heated periodically at 80° C. for 1 minute in every 24 hours. As shown in line 13 of FIG. 4, the component loses its deodorizing effect significantly in the long run when the deodorizing element is not treated for revitalizing. However, as shown by line 14 and line 15 of FIG. 4, it can maintain its effect at a high level when it is periodically subjected to a treatment for revitalizing the deodorizing element.

Still another embodiment of the present invention is described below. A porous block of sintered iron was prepared using powdered iron with an average particle size of 5 $\mu$m in a similar manner as described above. The obtained porous block was then immersed in a solution containing L-ascorbic acid at a concentration of 0.5 mol/l and gluconic acid at a concentration of 0.5 mol/l at a temperature of 60° C. for 15 minutes and dried in the atmosphere. An emulsion of $Ca(OH)_2$ and ethanol was then sprayed on its surface. The deodorizing elements of the present invention, thus obtained, were set in an apparatus. The component was set in a small room, where more than 20 cigarettes were smoked every day. A tentilator was arranged so that clean air was supplied to the deodorizing element for 3 minutes following every ventilating operation. During the 2 years in which the experiment was conducted, the air was always kept clean and the content of the substances contained in the air was as follows: $H_2S$:0.1 ppm, $NH_3$:0.1 ppm, 5Ox:1 ppm, $NO_2$:0 ppm, $CO_2$:50 ppm, CO:3 ppm, acetaldehyde:0 ppm. As is apparent from the above description, the component of the present invention can maintain its deodorizing effect at its initial level over a long period of use without the need to replace its deodorizing element.

What is claimed is:

1. A deodorizing unit comprising (1) a sintered, porous block of a metal selected from at least one of Fe, Mn, Cr, Ni, Zn, Al and Cu, and (2) a reaction product of said metal and an acid selected from at least one of ascorbic acid, gluconic acid, citric acid, tartaric acid, tannic acid, gallic acid, EDTA and malic acid, said reaction product being coated on said metal.

2. The deodorizing unit of claim 1, further comprising at least one basic salt selected from CaO, MgO, Ca(OH)$_2$, Mg(OH$_2$, $CaCO_3$, $MgCO_3$, and $Na_2CO_3$ on the surface of said reaction product.

3. The deodorizing unit of claim 1, further comprising active carbon mixed with said reaction product.

4. The deodorizing unit of claim 1, further comprising a heater positioned so as to heat said block.

5. The deodorizing unit of claim 4, wherein said heater is an electric resistance heater.

6. The deodorizing unit of claim 4, wherein said heater is an electromagnetic induction heater.

7. The deodorizing unit of claim 1, further comprising a source of steam positioned so as to provide steam to said block.

8. The deodorizing unit of claim 7, wherein said source of steam comprises an ultrasonic humidifier.

9. The deodorizing unit of claim 7, wherein said source of steam comprises a heater-steam generator.

10. The deodorizing unit of claim 4, further comprising a source of steam positioned so as to provide steam to said block.

11. The deodorizing unit of claim 10, wherein said source of steam comprises an ultrasonic humidifier.

12. The deodorizing unit of claim 10, wherein said source of steam comprises a heater-steam generator.

13. A method of restoring the deodorizing effect of a deodorizing unit comprising the step of:
passing clean air or gas through a deodorizing unit;
wherein said unit comprises (1) a sintered, porous block of a metal selected from at least one of Fe, Mn, Cr, Ni, Zn, Al and Cu, and (2) a reaction product of said metal and an acid selected from at least one of ascorbic acid, gluconic acid, citric acid, tartaric acid, tannic acid, gallic acid, EDTA and malic acid, said reaction product being coated on said metal.

14. The method of claim 13, further comprising the step of heating said block.

15. The method of claim 13, further comprising the step of moistening said block.

16. The method of claim 14, further comprising the step of moistening said block.

17. The method of claim 13, wherein said gas is steam, or a mixture of steam and air.

18. The method of claim 13, wherein said step of passing is carried out once every 15 days.

19. The method of claim 13, wherein said step of passing is carried out once every 25 days.

20. The method of claim 18, wherein said step of passing is conducted for 5 minutes.

* * * * *